United States Patent [19]
Saadat

[11] Patent Number: 5,879,347
[45] Date of Patent: Mar. 9, 1999

[54] APPARATUS FOR CONTROLLED THERMAL TREATMENT OF TISSUE

[75] Inventor: Vahid Saadat, Redwood Shores, Calif.

[73] Assignee: Gynecare, Inc., Menlo Park, Calif.

[21] Appl. No.: 845,764

[22] Filed: Apr. 25, 1997

[51] Int. Cl.$^6$ .................................................. A61B 17/38
[52] U.S. Cl. ................................ 606/28; 606/27; 606/29; 606/31; 606/41; 606/42; 606/48; 606/194; 604/113; 604/114; 607/101
[58] Field of Search ................................ 606/27–29, 31, 606/41–42, 48–50, 194; 604/96–99, 113–114; 607/101–105

[56] References Cited

U.S. PATENT DOCUMENTS

| | | | |
|---|---|---|---|
| 4,116,201 | 9/1978 | Shah | 604/99 |
| 4,793,351 | 12/1988 | Landman | 604/99 |
| 5,498,261 | 3/1996 | Strul | 606/29 |

*Primary Examiner*—Robert L. Nasser
*Assistant Examiner*—Michael Astorino
*Attorney, Agent, or Firm*—Emil Richard Skula

[57] ABSTRACT

An apparatus for treating body tissue using controlled application of heat includes an catheter having an expandable device defining a fluid reservoir about the distal end of the catheter. Fluid is provided to the fluid reservoir through a fluid supply conduit, and fluid drains from the fluid reservoir via a fluid drainage conduit. The apparatus includes a first pressure control valve that controls the outflow of fluid through the fluid drainage conduit, so that fluid pressure within the fluid reservoir is maintained within a desired range. The apparatus may also include a second pressure control valve that drains the fluid reservoir in case of an overpressure, such as may occur upon failure of the first pressure control valve. The apparatus may also include an electrical heating element disposed at the distal end of the catheter within the fluid reservoir, with current flow through heating element controlled by simple temperature switches that are also disposed at the distal end of the catheter within the fluid reservoir.

7 Claims, 2 Drawing Sheets

APPARATUS FOR CONTROLLED THERMAL TREATMENT OF TISSUE

BACKGROUND OF THE INVENTION

1. Field of the Invention

The invention relates to a device for controlling the temperature and pressure of fluid within a container used to thermally treat body tissue. More particularly, the present invention relates to an expandable device filled with fluid, with a heating assembly and pressure control valve within the expandable device.

2. Description of Related Art

Application of thermal energy has been used for some time to treat body tissues. One method of controlled application of thermal energy involves the use of a balloon or similar container filled with fluid at an elevated temperature and pressure. The balloon is placed against the tissue to be treated, and the heat from the fluid is conducted through the walls of the balloon and into the tissue.

Application of thermal energy with fluid-filled balloons has been of particular use in treating tissue in body cavities of animals, including humans. For example, balloons filled with heated fluid have been used to effect coagulation and/or cauterization of a uterine endometrium.

A method is known for effecting necrosis of the endometrium by inserting a distensible bladder into the uterus. The distensible bladder is inflated to a predetermined pressure with a fluid so that the distensible bladder is in contact with substantially all of the tissue lining for which necrosis is desired. The fluid is heated to a temperature sufficient to coagulate and/or ablate the tissue lining. The temperature and pressure of the fluid is controlled by means connected to the distensible bladder. The bladder is maintained inflated with the fluid at a temperature for a period of time sufficient to effect necrosis of the endometrium.

Early methods for heated-balloon therapy required the fluid to be preheated outside the body, and then pumped through conduits into the balloon or other bladder. Another method for heated-balloon therapy involves positioning a heating element coil in the balloon, and causing an electrical current to pass through the coil, thereby heating the coil and the surrounding fluid. Such heating systems require accurate temperature monitoring and control. Various temperature monitoring and control systems are known in the art, but many temperature control systems are relatively expensive and of varying reliability.

Controlling the pressure within the balloon is another concern, particularly in gynecological and other endoscopic procedures. Pressure control is of particular concern to prevent overinflation, and possibly bursting, of the balloon. External pressure monitors are known in the art, but can be relatively expensive.

Consequently, there is a need to improve heated, pressurized fluid systems to provide effective control of the fluid temperature and pressure while at the same time allowing for reduced system cost. The present invention satisfies these needs.

SUMMARY OF THE INVENTION

Briefly and in general terms, the present invention provides an apparatus for heating fluid in a cavity. More particularly, the present invention is a device for controlling temperature and pressure within a fluid-filled expandable device such as a balloon.

The present invention is useful for applying heat to body tissue, such as is necessary to achieve endometrial ablation. The apparatus provides for heating of an inflation medium within a distensible bladder positioned adjacent to the tissue to be treated. The invention has particular application in providing a safe and efficacious method for ablating the endometrium of the uterus. The present invention thus provides a relatively inexpensive and easy method to treat menorrhagia in women.

The invention is an apparatus for treating tissue at a selected operation site, including an expandable device defining a fluid reservoir, a supply conduit for delivering the fluid into the fluid reservoir, a discharge conduit for draining fluid from the fluid reservoir, and a first pressure control valve configured to automatically open the first discharge conduit when the pressure within the fluid reservoir reaches a first high threshold. The fluid reservoir may be mounted on a catheter for use within a body cavity such as the uterus.

In a particular embodiment, the first pressure control valve automatically closes when the pressure falls below a low threshold.

In a further embodiment, the device includes a second pressure control valve configured to open when the fluid pressure within the fluid reservoir reaches a second high threshold. In a particular embodiment, the second high threshold is higher than the first high threshold, and the second pressure control valve acts as an emergency backup control in case of failure or overwhelming of the first pressure control valve.

In a further embodiment, the second pressure control valve has an effective capacity/area greater than the effective capacity/area of the first pressure control valve. The second pressure control valve may open the first drainage conduit. In another embodiment, the second pressure control valve opens a second drainage conduit, which is separate from the first drainage conduit opened by the first pressure control valve.

In a particular embodiment, the second pressure control valve is a one-use pressure relief valve that cracks at the second high threshold.

In another embodiment of the invention, the apparatus comprises an expandable bladder defining a fluid reservoir therein, a supply conduit for delivering fluid into the fluid reservoir, a discharge conduit for draining fluid from the fluid reservoir, an electrical heat assembly positioned within the fluid reservoir, and an electrical power source in electrical contact with the heat assembly.

In a particular embodiment, the heat assembly is a heating element such as a thermal resistance coil that generates heat when an electrical current is passed therethrough.

In a further embodiment, the invention further includes a first temperature switch positioned within the fluid reservoir in electrical contact with the heat assembly, said first temperature switch controlling electrical flow through the heat assembly. The device may also include a second temperature switch positioned within the fluid reservoir in electrical contact with the electrode assembly, with the second temperature switch controlling electrical flow through the electrode assembly. The first and second temperature switches may be connected in series to form a doubleredundant system.

Other features and advantages of the present invention will become more apparent from the following detailed description of the invention when taken in conjunction with the accompanying drawings.

DETAILED DESCRIPTION OF THE PREFERRED EMBODIMENTS

Figure 1:
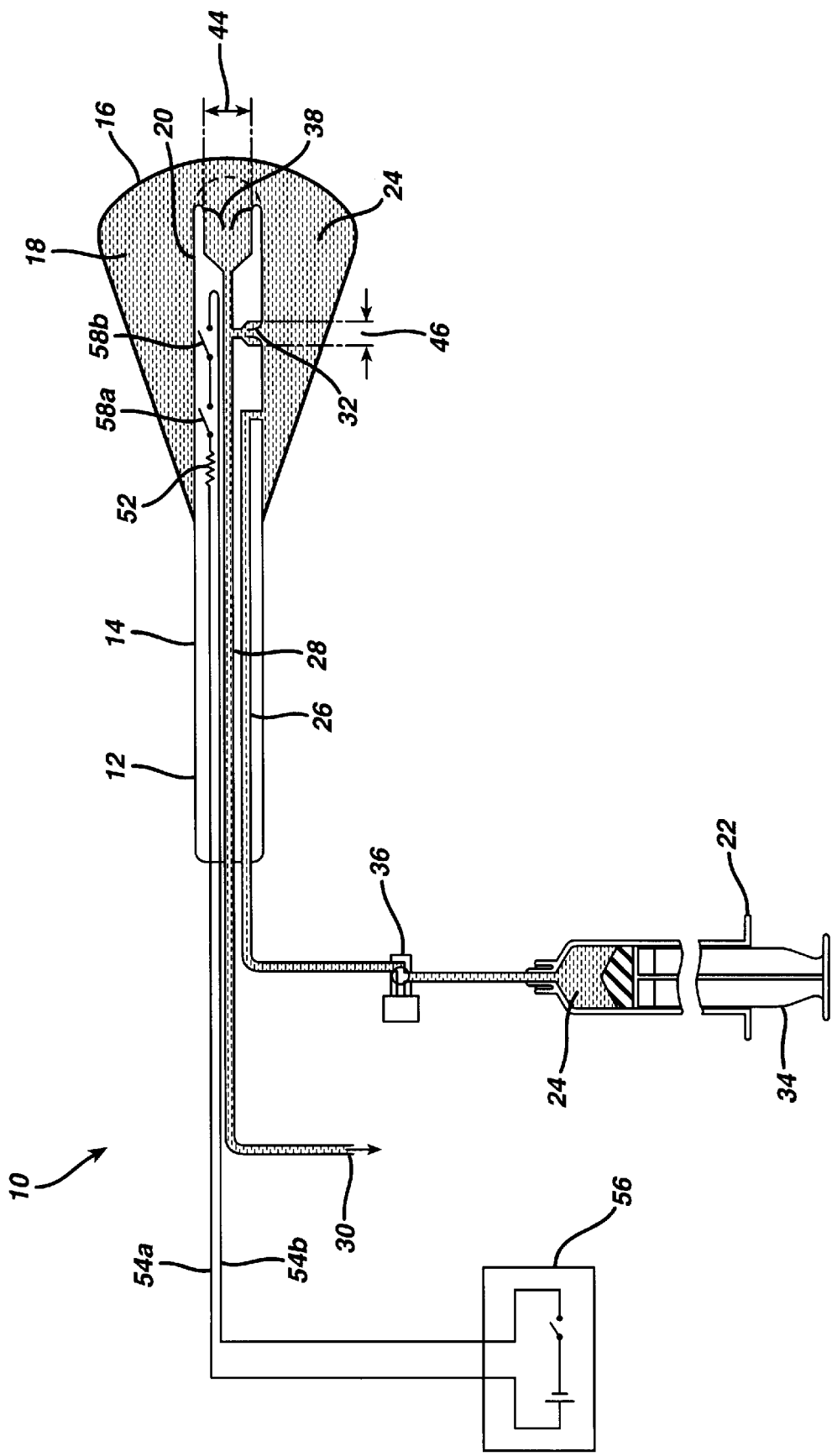
FIG. 1 is a side view, in cross section, of an apparatus according to one embodiment of the present invention, including a treatment catheter having a distensible bladder.
Figure 2:
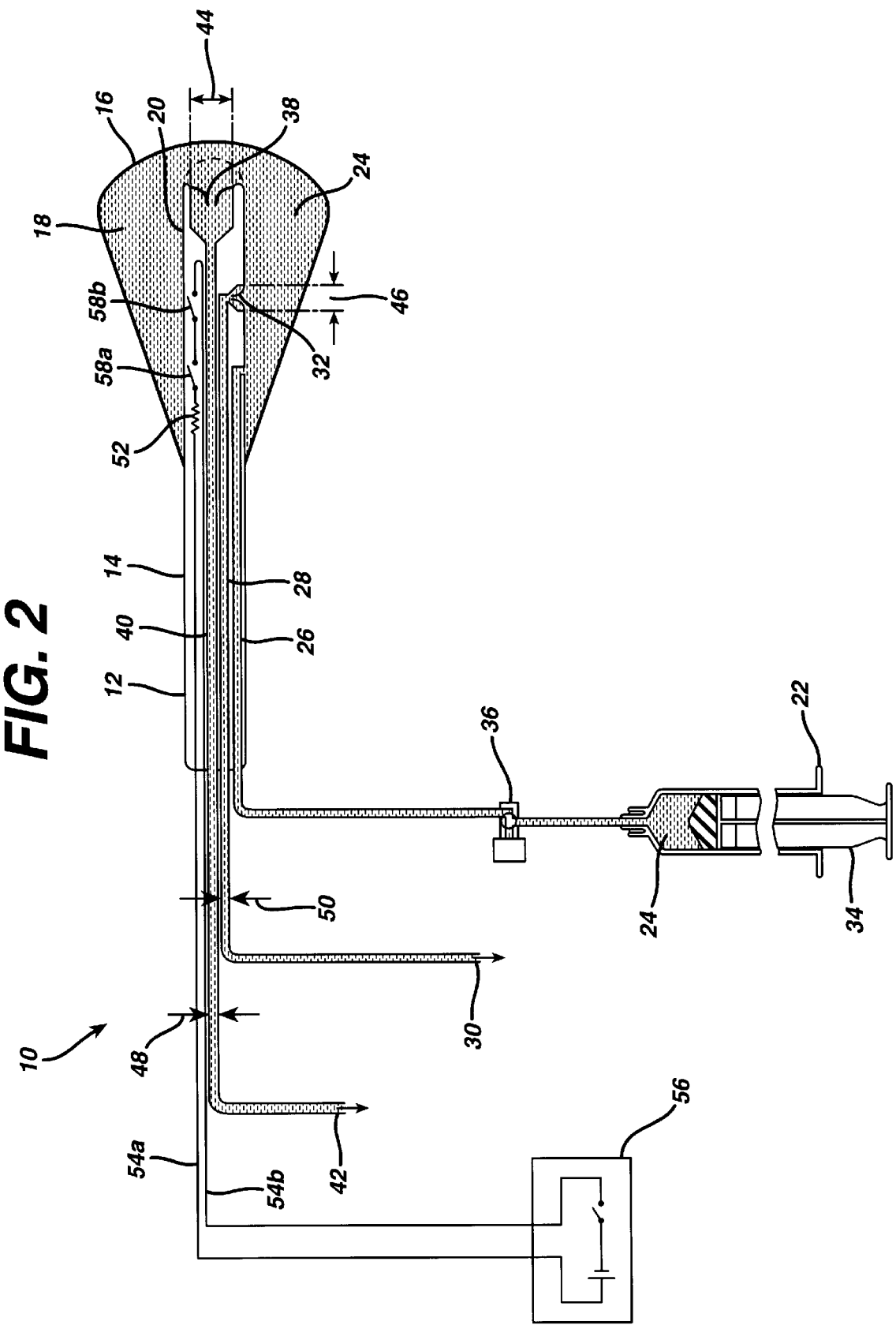
FIG. 2 is a side view, in cross section, of a heated bladder device according to another embodiment of the invention.

The present invention is depicted in FIGS. 1–2 for use in body cavities, including use in ablating the endometrial lining of a patient's uterus. However, the present invention is not limited to use in the uterus, and may be applied to techniques for thermal treatment of a variety of tissue, including the treatment of tissue within a variety of body cavities such as the urinary bladder, the gall bladder, portions of the gastrointestinal tract, the heart, and other body cavities. The invention may be used in a variety of procedures, including thermal treatment of hemorrhoids, intestinal walls, the lining of the rectum, the lining of the bladder, etc. Moreover, the invention may also be used for heating a pressurizing fluid in a variety of applications where controlled application of pressure and heat is desired, and not just for the treatment of tissue.

Referring now to FIG. 1, in one preferred embodiment the apparatus 10 of the invention comprises a catheter 12 including a generally elongated shaft 14 having a distensible bladder 16 or similar expandable device defining a fluid reservoir 18 at the shaft distal end 20. The bladder 16 may be formed of inelastic or elastic materials.

The fluid reservoir 18 is filled with fluid 24 provided by a syringe 22 or other fluid source. The syringe 24 is in fluid contact with the fluid reservoir via a fluid supply conduit 26.

In the embodiment shown in FIG. 1, the apparatus 10 includes a first drainage conduit 28 in fluid contact with the fluid reservoir 18, with the first drainage conduit leading to a primary fluid discharge port 30. Fluid access to the first drainage conduit 28 is controlled by a first pressure control valve 32.

During operation of the apparatus 10, fluid is introduced into the fluid reservoir 18. For example, where the fluid source is a manual syringe 22 such as that shown in FIG. 1, a user will depress the syringe piston 34, thereby causing fluid to flow from the syringe 22 through the supply conduit 26 to the fluid reservoir 18.

The first pressure control valve 32 is configured to open when fluid pressure within the fluid reservoir 18 reaches a threshold value. Accordingly, when the fluid pressure reaches that threshold, the first pressure control valve 32 will open and allow fluid to pass through the first drainage conduit 28 and out of the primary discharge port 30. The primary discharge port is preferably located so that it can be easily observed or otherwise monitored by the user. Thus, when a user observes fluid flowing from the primary discharge port 30, the user knows that fluid pressure within the fluid reservoir 18 has reached the desired pressure range.

The first pressure control valve 32 is preferably a of a type that opens at a high pressure threshold and closes at a low pressure threshold, such as a duck bill valve or a ball and spring valve. Accordingly, the first pressure control valve 32 can maintain the fluid pressure in the range defined by the high and low pressure thresholds.

In a preferred embodiment useful for gynecological applications, the high pressure threshold is approximately 200 mm Hg, and the low pressure threshold is approximately 150 mm Hg. Accordingly, the fluid pressure within the fluid reservoir 18 will be maintained in the range between 150 mm Hg and 200 mm Hg.

In a further embodiment, the high pressure threshold and low pressure thresholds are essentially identical, so that the pressure in the fluid reservoir 18 can be maintained with greater precision. In a particular embodiment, the high and low pressure thresholds may both be about 160 mm Hg, so that the fluid within the fluid reservoir can be maintained very close to 160 mm Hg.

The apparatus 10 may further include a flow control valve 36 that prevents unwanted flow between the fluid reservoir 18 and syringe 22. The flow control valve 36 may have different configurations. For example, the flow control valve 36 may have an inflation configuration that allows fluid to be pass from the syringe 22 into the fluid reservoir 18 but prevents fluid from passing back to the syringe 22 from the fluid reservoir 18. Thus, a user could depress the syringe 22 to fill the fluid reservoir 18 and, upon observing fluid flowing from the primary discharge port 30, release the syringe piston 34 without having fluid return from the fluid reservoir 18 to the syringe 22. Accordingly, the flow control valve 36 in inflation configuration, combined with the first pressure relief valve 32, maintains the fluid pressure within the fluid reservoir 18 within a desired pressure range.

The flow control valve 36 may also have a deflation configuration that allows fluid to pass from the fluid reservoir 18 to the syringe 22 but prevents fluid from passing from the syringe 22 into the fluid reservoir 18. The flow control valve 36 may also have a closed configuration, wherein fluid may not pass in either direction between the fluid reservoir 18 and syringe 22, as well as an entirely open configuration, wherein fluid may pass freely in both directions between the fluid reservoir 18 and the syringe 22.

The apparatus 10 may further include a second pressure control valve 38. The second pressure control valve 38 opens when pressure within the fluid reservoir exceeds a second high threshold. In one embodiment, the second high threshold is higher than the first high threshold of the first pressure control valve, so that the second pressure control valve 38 acts as an emergency relief valve that opens only when the first pressure control valve 32 fails, is blocked, or is overwhelmed by a sudden fluid overpressure.

In one embodiment, the second pressure control valve 38 is a one-use relief or actuated valve that permanently opens, such as by cracking of a seal, at the second high threshold. Such a one-use valve will not reclose itself if and when the pressure subsequently drops below the threshold. Upon activation of such a one-use valve, the fluid reservoir can no longer hold substantial fluid pressure, so that further fluid pressurization of the fluid reservoir 18 is prevented. Thus, when a one-use second pressure control valve becomes cracked, the user cannot maintain pressure in the fluid reservoir 18 and must remove and replace the apparatus 10. A one-use second pressure control valve thus prevents use of the apparatus 10 where the first pressure control valve 32 has failed.

In the embodiment shown in FIG. 1, the second pressure control valve 38, when open, admits fluid from the fluid reservoir 18 to the first drainage conduit 28 and thus to the primary discharge port 30. Large amounts of fluid discharging from the primary discharge port 30 would indicate that the second pressure control valve 38 has been activated, thus indicating failure of the first pressure control valve 32 to maintain the pressure below the first high threshold.

In the embodiment shown in FIG. 2, the second pressure control valve 38 admits fluid 24 from the fluid reservoir 18 to a second drainage conduit 40 and thus to a secondary discharge port 42. Thus, even if the first drainage conduit 28 becomes blocked or otherwise fails to properly drain fluid, the second pressure control valve 38 can still drain fluid 24 from the bladder 16 through the second drainage conduit 40. In such an embodiment, the secondary discharge port 42 may be configured so that a user may easily see or otherwise observe fluid passing therefrom. Any amount of fluid 24 discharging from the secondary discharge port 42 indicates that an overpressure had occurred, which may indicate failure, blockage, or overwhelming of the first pressure control valve 32 and/or first drainage conduit 28. The user, upon observing discharge from the secondary discharge port 42, thus knows to expedite drainage of the fluid reservoir 18 and remove the catheter 12 for replacement and/or inspection.

In the embodiment of FIG. 2, the second pressure control valve width 44 is larger than the first pressure control valve width 46, and the second drainage conduit width 48 is larger than the first drainage conduit width 50. Thus, the second pressure control valve 38 has a larger intake area and drainage capacity than the first pressure control valve 32. Opening of the second pressure control valve 38 allows greater amounts of fluid to drain than does opening of the first pressure control valve 32.

The enlarged intake area of the second pressure control valve 38 allows for rapid deflation of the fluid reservoir where overpressure occurs. The enlarged intake area can also allow larger particles to pass therethrough. For example, in the unlikely event that an undesired particle is present in the fluid 24 in the fluid reservoir 18, and the particle blocks the first pressure control valve 32, the larger size of the second pressure control valve 38 may allow the particle to pass therethrough.

As shown in FIG. 1, the apparatus may also include a heating element 52 disposed at the distal end of the catheter 12 within the expandable bladder 16. The heating element 52 may include a resistance coil or similar structure in electrical contact via electrical leads 54a, 54b with an electrical power source 56. When current passes through the heating element 52, the heating element 52 produces heat which is transmitted to the fluid 24 in the fluid reservoir 18.

In the embodiment shown in FIG. 1, current flow through the heating element 52 is controlled by one or more temperature switches 58a, 58b. When the fluid temperature is below an activation temperature, the temperature switches 58a, 58b close to allow current to pass from the electrical power source 56 through the heating element 52. When the fluid temperature reaches the activation temperature, the switches 58a, 58b open, thereby preventing current from flowing through the heating element 52 until the temperature again falls below the activation temperature. By having multiple temperature switches 58a, 58b connected in series, a redundant temperature control system is created whereby failure of one of the switches 58a, 58b will not result in overheating of the fluid 24.

In a particular embodiment, the activation temperatures of the temperature switches 58a, 58b are set during manufacture of the device. The catheter 12 is sealed during manufacture, thereby preventing subsequent access to and modification of the temperature switches 58a, 58b. Thus, the temperature range is preselected and cannot be modified by the user. Because the temperature of certain applications, such as endometrial ablation, is well established, such temperature ranges can be preset in the apparatus during manufacture, so that a user does not have to make any adjustments thereto.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. An apparatus for treating tissue at a selected operation site, the apparatus comprising:

an expandable device defining a fluid reservoir therein for holding a fluid;

a supply conduit in fluid communication with the fluid reservoir for delivering the fluid into the fluid reservoir;

a first discharge conduit in fluid communication with the fluid reservoir for draining fluid from the fluid reservoir;

a first pressure control valve on the discharge conduit configured to automatically open the discharge conduit when the fluid pressure within the fluid reservoir reaches a first threshold;

a second pressure control valve on the first discharge conduit configured to automatically open when the fluid pressure within the fluid reservoir reaches a second threshold;

a second discharge conduit in fluid communication with the fluid reservoir for draining fluid from the fluid reservoir; and a second pressure control valve on the second discharge conduit configured to automatically open when the fluid pressure within the fluid reservoir reaches a second threshold, wherein the second pressure threshold is higher than the first pressure threshold, and wherein the first pressure control valve and the second pressure control valve each have an intake area, and the intake area of the second pressure control valve is larger than the intake area of the first pressure control valve.

2. The apparatus of claim 1, further comprising:

an electrode assembly positioned within the expandable device; and an electrical power source in electrical contact with the electrode assembly.

3. The apparatus of claim 1, further comprising:

a first temperature switch positioned within the expandable device in electrical contact with the electrode assembly, said first temperature switch controlling electrical flow through the electrode assembly.

4. The apparatus of claim 3, further comprising:

a second temperature switch positioned within the expandable device in electrical contact with the electrode assembly, said second temperature switch controlling electrical flow through the electrode assembly.

5. The apparatus of claim 4, wherein the first temperature switch and the second temperature switch are electrically connected in series.

6. An apparatus for treating tissue at a selected operation site, the apparatus comprising:

an elongated shaft having a distal end;

an expandable device at the distal end of the elongated shaft, the expandable device having an expandable reservoir therein for holding a fluid;

a supply conduit in fluid communication with the expandable reservoir for delivering the fluid into the expandable reservoir;

a first discharge conduit in fluid communication with the expandable reservoir for draining fluid from the expandable reservoir;

a first pressure control valve on the discharge conduit configured to automatically open the discharge conduit when the pressure within the expandable device reaches a first threshold;

a second pressure control valve on the first discharge conduit configured to automatically open when the pressure within the expandable device reaches a second threshold;

a second discharge conduit in fluid communication with the expandable reservoir for draining fluid from the expandable reservoir; and, a second pressure control valve on the second discharge conduit configured to automatically open when the pressure within the expandable device reaches a second threshold, wherein the second pressure threshold is higher than the first pressure threshold, and wherein the first pressure control valve has an intake area and the second pressure control valve has an intake area, and the second pressure control valve intake area is larger than the first pressure control valve intake area.

7. An apparatus for treating tissue at a selected operation site, the apparatus comprising:

an elongated catheter having a distal end;

an expandable device about the elongated catheter distal end, the expandable device defining an expandable fluid reservoir about the catheter distal end;

a supply conduit in fluid communication with the expandable reservoir for delivering fluid into the expandable fluid reservoir;

a heating element positioned at the catheter distal end within the fluid reservoir;

an electrical power source in electrical contact with the electrode assembly;

a first temperature switch positioned at the catheter distal end in electrical contact with the heating element, said first temperature switch controlling electrical flow through the heating element;

a discharge conduit in fluid communication with the fluid reservoir for draining fluid from the fluid reservoir;

a first pressure control valve on the discharge conduit configured to automatically open the discharge conduit when the fluid pressure within the fluid reservoir reaches a first threshold; and a second pressure control valve on the discharge conduit configured to automatically open when the fluid pressure within the fluid reservoir reaches a second threshold;

a second temperature switch positioned at the catheter distal end in electrical contact with the heating element, said second temperature switch controlling electrical flow through the heating element, wherein the first temperature switch and the second temperature switch are electrically connected in series, and wherein the heating element comprises a resistance coil configured to generate heat when an electrical current passes therethrough.

* * * * *